United States Patent
Baruto et al.

(10) Patent No.: US 9,115,124 B1
(45) Date of Patent: Aug. 25, 2015

(54) PROCESS AND INTERMEDIATES FOR THE PREPARATION OF DASATINIB

(71) Applicant: CERBIOS-PHARMA SA, Barbengo/Lugano (CH)

(72) Inventors: Alessandro Baruto, Tromello (IT); Mauro Gaboardi, Novara (IT); Marta Castaldi, Sizzano (IT); Graziano Castaldi, Briona (IT)

(73) Assignee: CERBIOS-PHARMA SA, Barbengo/Lugano (CH)

( * ) Notice: Subject to any disclaimer, the term of this patent is extended or adjusted under 35 U.S.C. 154(b) by 0 days.

(21) Appl. No.: 14/631,956

(22) Filed: Feb. 26, 2015

(30) Foreign Application Priority Data

Mar. 11, 2014 (IT) .............................. MI2014A00376

(51) Int. Cl.
*C07D 417/12* (2006.01)
*C07D 417/14* (2006.01)

(52) U.S. Cl.
CPC ............ *C07D 417/12* (2013.01); *C07D 417/14* (2013.01)

(58) Field of Classification Search
CPC .................................................... C07D 417/12
USPC ........................................................ 544/295
See application file for complete search history.

(56) References Cited

U.S. PATENT DOCUMENTS

| 7,652,146 B2 | 1/2010 | Chen et al. |
| 2006/0069101 A1 | 3/2006 | Kim et al. |
| 2007/0219370 A1 | 9/2007 | Sun et al. |

FOREIGN PATENT DOCUMENTS

| EP | 1711481 | 10/2006 |
| EP | 2532662 | 12/2012 |
| WO | 0062778 | 10/2000 |
| WO | 2005077945 | 8/2005 |
| WO | 2011009226 | 1/2011 |

OTHER PUBLICATIONS

Database Registry Chemical Abstracts Service, Columbus, Ohio, US, XP002727365, Apr. 21, 2006, Database accession No. 881381-54-0.
Database Registry Chemical Abstracts Service, Columbus, Ohio, US, XP002727366, Apr. 21, 2006, Database accession No. 881381-56-2.
Database Registry Chemical Abstracts Service, Columbus, Ohio, US, XP002727367, Apr. 21, 2006, Database accession No. 881381-60-0.
Database Registry Chemical Abstracts Service, Columbus, Ohio, US, XP002727368, Apr. 21, 2006, Database accession No. 881381-51-7.
Liu, Fei, et al., Synthesis and Biopharmaceutical Studies . . . , Chem. Pharm. Bull., vol. 61, No. 8, pp. 877-881, 2013.
European Search Report corresponding to IT priority application MI2014A000376, Jul. 18, 2014.

*Primary Examiner* — Taofiq A Solola
(74) *Attorney, Agent, or Firm* — Lucas & Mercanti LLP

(57) ABSTRACT

The present invention relates to a process for the synthesis of dasatinib and to intermediates useful for its preparation.

9 Claims, No Drawings

PROCESS AND INTERMEDIATES FOR THE PREPARATION OF DASATINIB

CROSS-REFERENCE TO RELATED APPLICATIONS

This application claims the benefit of priority from Italian Patent Application Serial No. MI2014A000376, filed Mar. 11, 2014, the contents of which are incorporated herein by reference.

FIELD OF THE INVENTION

The present invention relates to a process for the synthesis of dasatinib and to intermediates useful for its preparation.

BACKGROUND OF THE INVENTION

Dasatinib belongs to a new class of targeted antitumoral drugs, the inhibitors of the tumoral growth; in particular it is an inhibitor of the tyrosine-kinase activity of BRC-ABL and further four oncogenic kinases which is mainly used in the treatment of chronic myelogenous leukemia (CML).

Chronic myelogenous leukemia (CML) is a myeloproliferative disease, caused by the anomalous growth of pluripotent hemopoietic stem cells, i.e. still able to proliferate and differentiate; these cells, as indicated by the adjective "myelogenous", belong at first to the series leading to the formation of granulocytes, a type of white blood cells, but it may also be related to other cell series. The phases of the untreated disease are three: the initial or chronic phase, generally with a slow course, which length is from three to five years from the diagnosis; the accelerated phase which is observed in about the 2/3 of the patients with a length of two-fifteen months; the blastic phase, associated with an average survival of three-six months, which inevitably leads to death. In most of the patients it seems that CML is caused by the reciprocal translocation of DNA segments between the chromosomes 9 and 22, with formation of the so-called Philadelphia chromosome (Ph), corresponding to a chromosome 22 in which the fusion BCR-ABL gene was formed and code for a protein that makes the blastos "immortal".

Dasatinib inhibits the activity of BCR-ABL through the competition with the ATP for the binding site on the tyrosine-kinase portion of the target protein of which the catalytic activity is inhibited, with the consequent block of the signal translation, so controlling the proliferation of the leukemia cells. Dasatinib is mainly used for the treatment of the patients who no longer respond to the treatment with imatinib.

Dasatinib is a compound of formula I

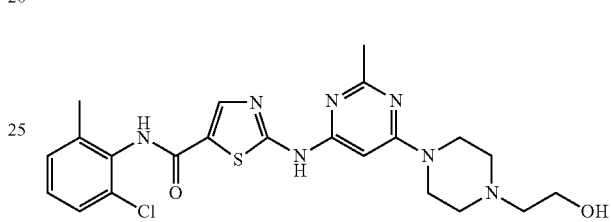

chemically known as N-(2-chloro-6-methylphenyl)-2-[6-[4-(2-hydroxyethyl)piperazin-1-yl]-2-methylpyrimidin-4-ylamino]thiazol-5-carboxamide, described in WO 00/62778 and sold under the name Sprycel®.

Some processes for the preparation of dasatinib are known in the prior art. WO 00/62778 discloses a process for the synthesis of dasatinib as reported in the following scheme 1.

Scheme 1

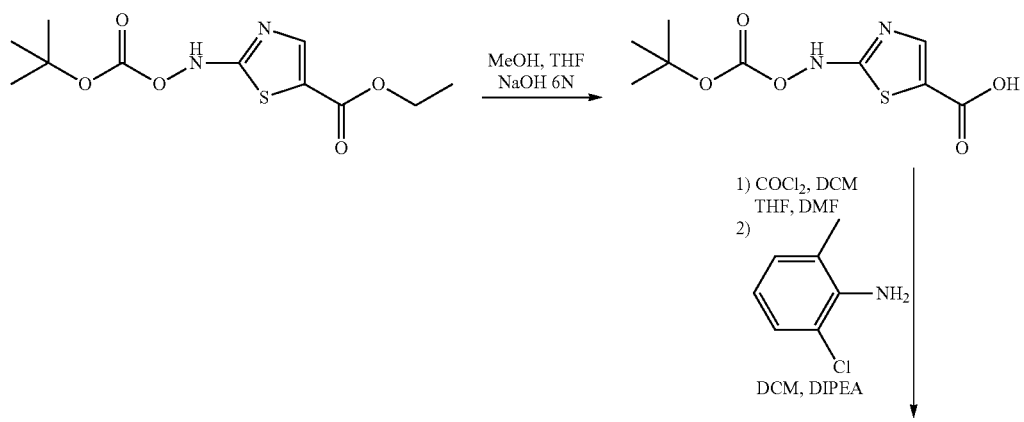

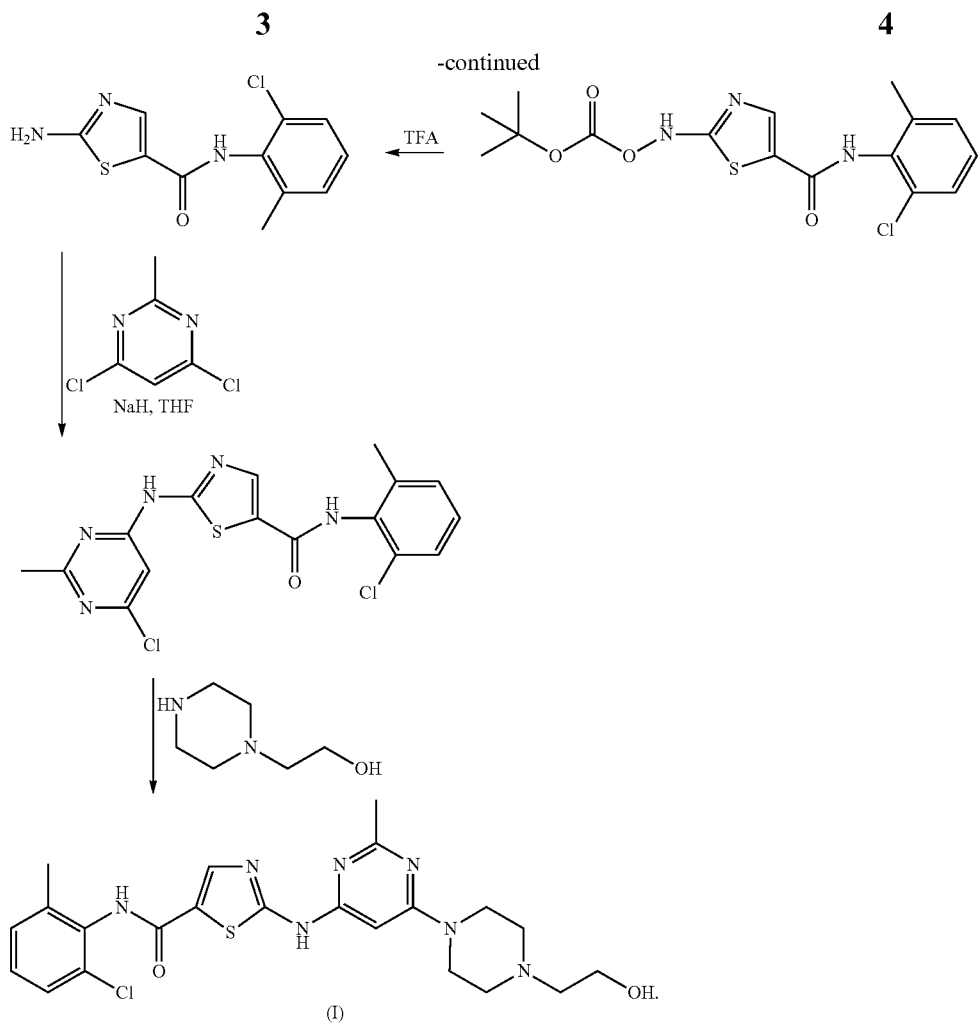
EP 1 711 481 discloses a process for the synthesis of dasatinib as reported in the following scheme 2.
Scheme 2
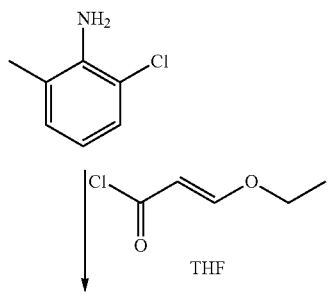

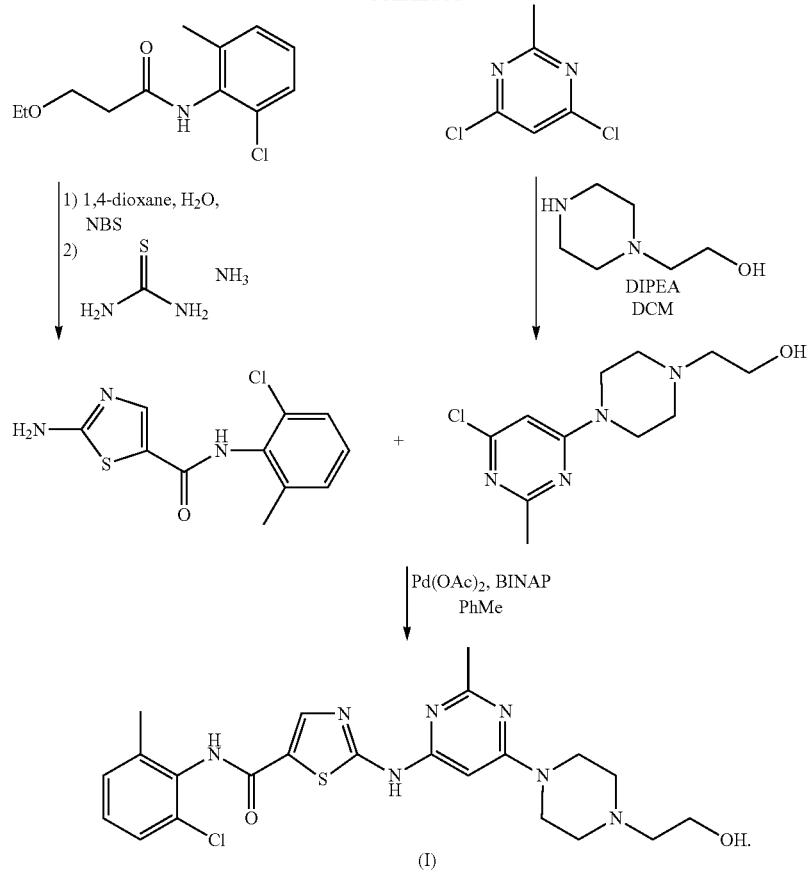
US 2007/219370 discloses a process for the synthesis of dasatinib as reported in the following scheme 3.
Scheme 3
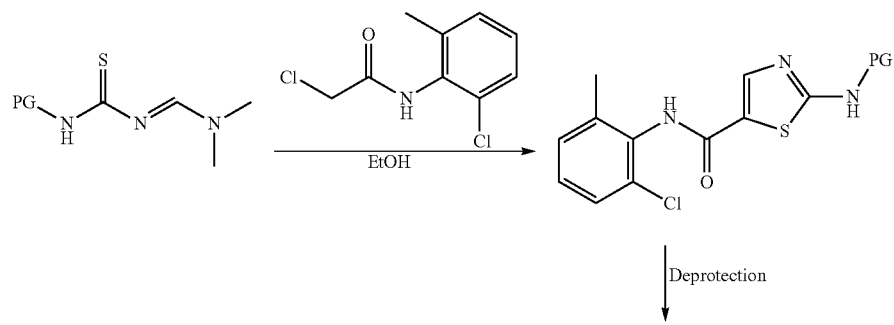

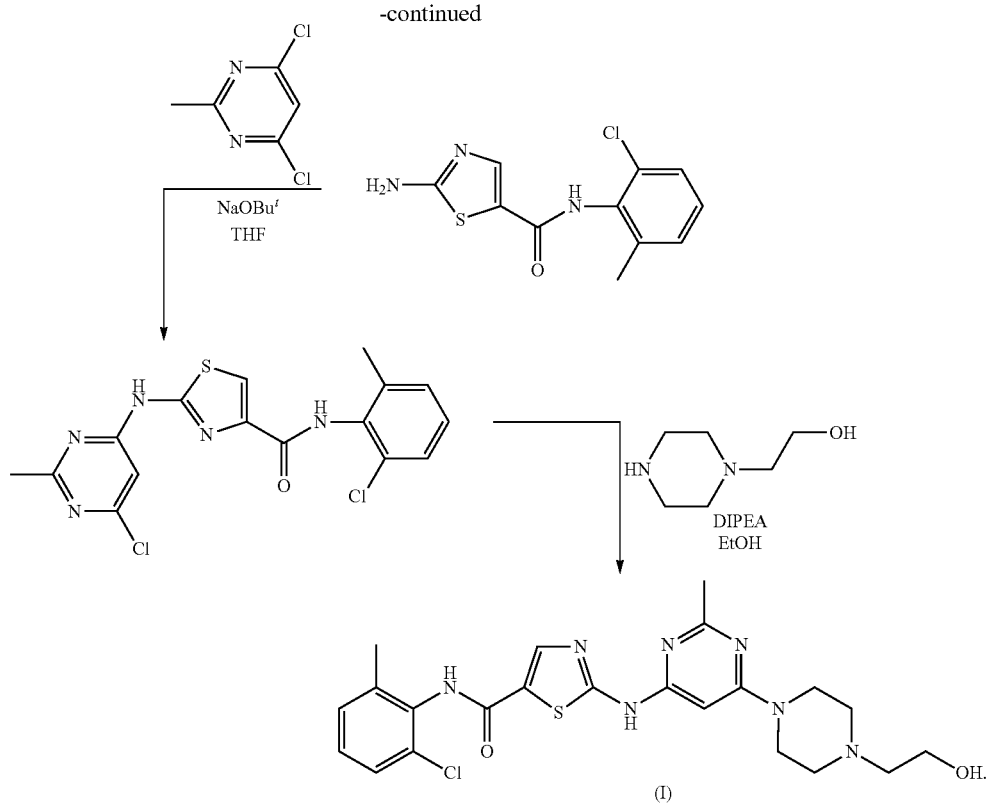
U.S. Pat. No. 7,652,146 discloses a process for the synthesis of dasatinib as reported in the following scheme 4.
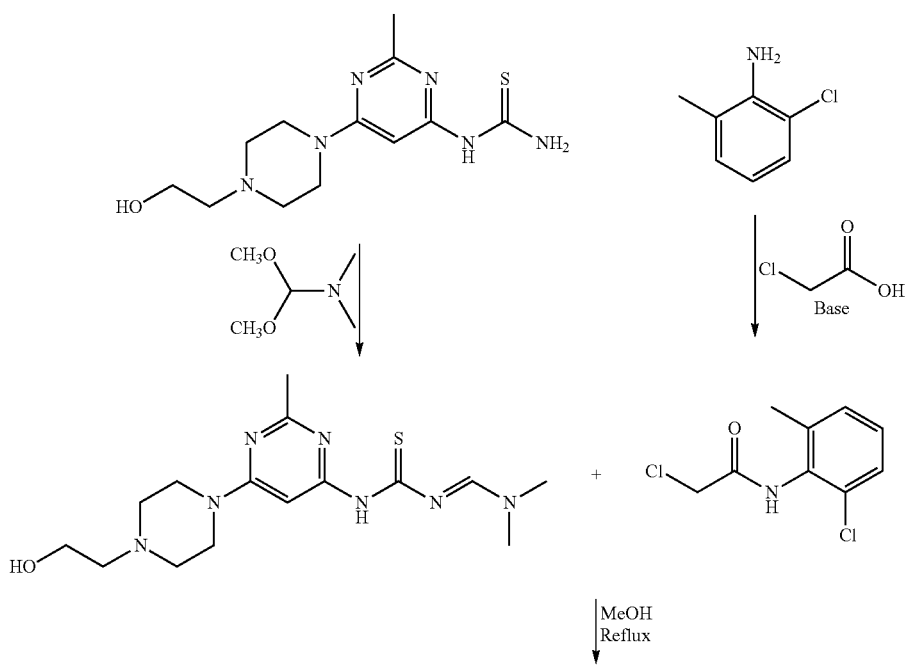

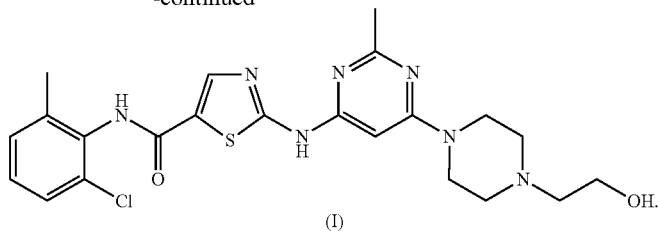

(I)

The processes known in the art involve reagents difficult to handle and with high environmental impact. Moreover, most of the processes described in the prior art include convergent or cyclization reactions which often lead to a decrease in the yields.

There is, therefore, the need to find a new process for the preparation of dasatinib which uses simple reactions with low environmental impact and which allows the use of cheap reagents which are easy to find on the market.

Therefore, an object of the present invention is a process for the preparation of dasatinib which uses cheap and with low environmental impact reagents easy to find on the market.

The process for the synthesis of dasatinib, which is an object of the present invention, comprises:

a) the reaction of the compound of formula X

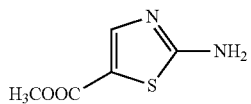

X with the compound of formula IX

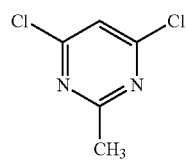

IX in an aprotic polar solvent and in the presence of a base, to give the compound of formula VIII

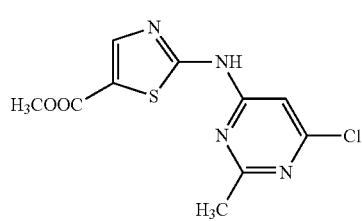

VIII b) the protection reaction of the compound of formula VIII to give a compound of formula VII

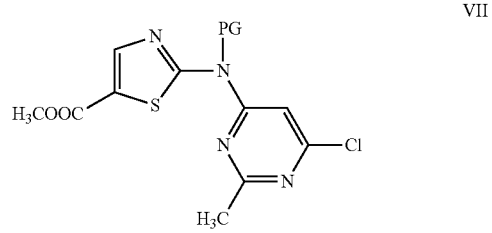

VII wherein PG is an amine protecting group;

c) the hydrolysis reaction of a compound of formula VII to give a compound of formula VI

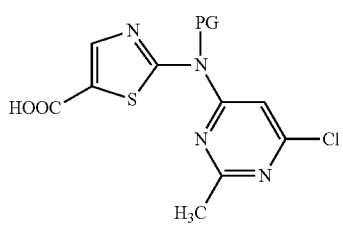

VI d) the reaction of a compound of formula VI with the compound of formula V

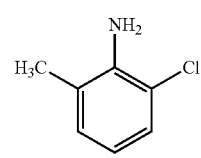

V to give a compound of formula IV

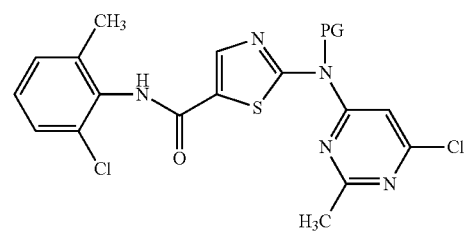

IV e) the coupling reaction of a compound of formula IV with the compound of formula III

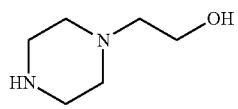

III in the presence of a base in a suitable solvent to give a compound of formula II

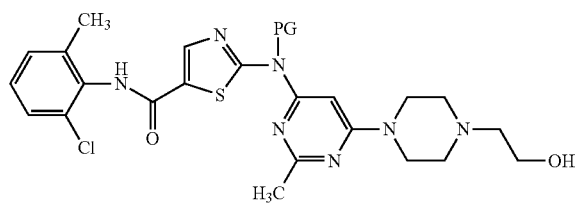

II and the simultaneous deprotection of said compound of formula II to give dasatinib of formula I or a salt thereof.

In step a) of the process of the present invention, the aprotic polar solvent is preferably selected from among N-methylpyrrolidone, dimethylacetamide, dimethylformamide, tetrahydrofuran, methyl-tetrahydrofuran or mixtures thereof. Dimethylacetamide is preferably used.

In step a) of the process of the present invention the base is preferably selected from among sodium hydride, potassium hydride, and lithium hydride. Sodium hydride is preferably used.

In step b) of the process of the present invention, PG is preferably selected from among a ter-butoxycarbonyl (BOC), methoxymethyl (MOM), trifluoroacetyl, acetyl, and triphenylmethyl (trityl). Ter-butoxycarbonyl is more preferably used.

The introduction of the protecting group is carried out through the reaction with a suitable reagent such as for example diter-butyl dicarbonate, triphenylmethyl chloride, acetyl chloride, acetic anhydride, etc.; in the presence of a base in a suitable polar or apolar solvent or mixtures thereof. The base used is preferably selected from among N,N-dimethylaminopyridine (DMAP), 1,5,7-triazabicyclo[4.4.0]dec-5-ene (TBD), 1,4-diazabicyclo[2.2.2]octane (DABCO), and 1,5-diazabicyclo[5.4.0]undec-5-ene (DBU). Still more preferably, the base is N,N-dimethylaminopyridine (DMAP). The polar solvent is preferably selected from among tetrahydrofuran, methyl-tetrahydrofuran, acetonitrile, dimethylformamide, dimethylacetamide, N-methylpyrrolidone, dimethylsulfoxide or mixtures thereof, while the apolar solvent is preferably selected from among toluene, xylene or mixtures thereof. Tetrahydrofuran is the solvent preferably used.

In step c) of the process of the present invention the hydrolysis is carried out in the presence of a base, preferably an inorganic base selected from among lithium hydroxide, sodium hydroxide and sodium carbonate, still more preferably lithium hydroxide, in a polar aprotic solvent preferably selected from among tetrahydrofuran, dimethylsulfoxide, N-methylpyrrolidone, dimethylformamide, and dimethylacetamide. Still more preferably the polar aprotic solvent is tetrahydrofuran.

Step d) of the process of the present invention is carried out through an intermediate of formula VIa

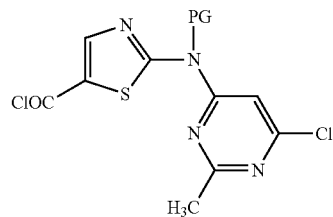

VIa wherein PG is an amine protecting group and has the above reported meanings; obtained by reacting a compound of formula VI with an organic tertiary amine, preferably selected from among triethylamine (TEA), pyridine, N,N-dimethylaminopyridine (DMAP), and N,N-diisopropylethylamine (DIPEA), still more preferably triethylamine, followed by the reaction with a chlorinating agent preferably selected from among oxalylchloride and tionylchloride, in an apolar solvent preferably selected from among methylene chloride, xylene or mixtures thereof. Tionyl chloride in methylene chloride is still more preferably used. The compound VIa is not isolated but is directly used in the subsequent step e).

The reaction between the compound of formula VIa and the compound of formula V is carried out in an apolar solvent preferably selected from among methylene chloride, xylene or mixtures thereof; with methylene chloride still more preferably used.

Step e) of the process of the present invention is carried out in the presence of a base preferably selected from among sodium carbonate, sodium bicarbonate, potassium carbonate, and potassium bicarbonate. Still more preferably, the base is sodium carbonate. The solvent is an aprotic polar solvent preferably selected from among tetrahydrofuran, dimethylsulfoxide, N-methylpyrrolidone, dimethylformamide, and dimethylacetamide, and still more preferably is dimethylsulfoxide.

Under these conditions also the simultaneous deprotection of the compound of formula II, which is then not isolated in the process of the present invention, is obtained.

The compounds of formula VII, VI, VIa, IV and II are new intermediates useful for the synthesis of dasatinib and therefore are a further object of the present invention.

In a preferred embodiment, the process for the synthesis of dasatinib comprises:

a) the reaction of the compound of formula X

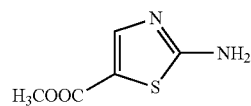

X with the compound of formula IX

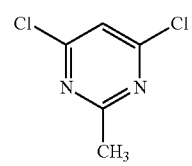

IX in an aprotic polar solvent and in the presence of a base, to give the compound of formula VIII

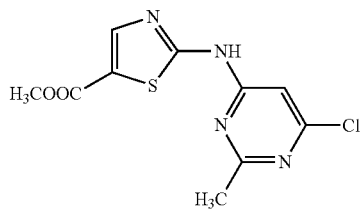

b) the protecting reaction of the compound of formula VIII to give the compound of formula VII

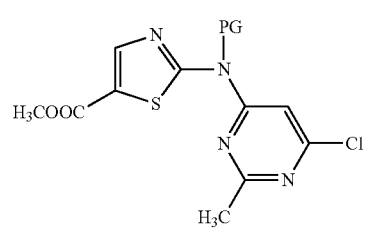

wherein PG is ter-butoxycarbonyl;

c) the hydrolysis reaction of the compound of formula VII to give the compound of formula VI

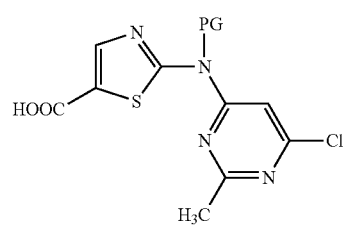

wherein PG is ter-butoxycarbonyl;

d) the reaction of the compound of formula VI with the compound of formula V

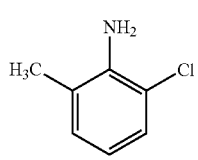

to give the compound of formula IV

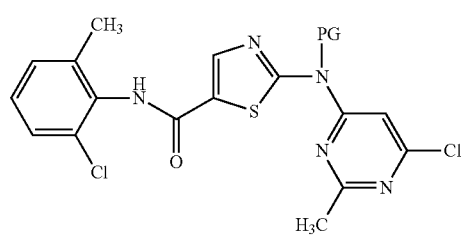

wherein PG is ter-butoxycarbonyl;

e) the coupling reaction of the compound of formula IV with the compound of formula III

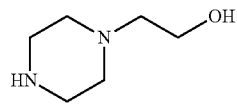

in the presence of a base in a suitable solvent to give the compound of formula II

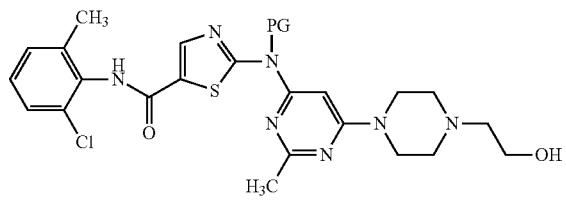

wherein PG is ter-butoxycarbonyl;

and the simultaneous deprotection of said compound of formula II to give dasatinib of formula I or a salt thereof.

In step a) of the process of the present invention, the aprotic polar solvent is preferably selected from among N-methylpyrrolidone, dimethylacetamide, dimethylformamide, tetrahydrofuran, methyl-tetrahydrofuran or mixtures thereof. Dimethylacetamide is preferably used.

In step a) of the process of the present invention the base is preferably selected from among sodium hydride, potassium hydride, and lithium hydride. Sodium hydride is preferably used.

The introduction of the protecting group ter-butoxycarbonyl is carried out through the reaction with a suitable reagent such as for example diter-butyl dicarbonate in the presence of a base in a suitable polar or apolar solvent or mixtures thereof. The base used is preferably selected from among N,N-dimethylaminopyridine (DMAP), 1,5,7-triazabicyclo[4.4.0]dec-5-ene (TBD), 1,4-diazabicyclo[2.2.2]octane (DABCO), and 1,5-diazabicyclo[5.4.0]undec-5-ene (DBU). Still more preferably, the base is N,N-dimethylaminopyridine (DMAP). The polar solvent is preferably selected from among tetrahydrofuran, methyl-tetrahydrofuran, acetonitrile, dimethylformamide, dimethylacetamide, N-methylpyrrolidone, dimethylsulfoxide or mixtures thereof, while the apolar solvent is preferably selected from among toluene, xylene or mixtures thereof. Tetrahydrofuran is the solvent preferably used.

In step c) of the process of the present invention, the hydrolysis is carried out in the presence of a base, preferably an inorganic base selected from among lithium hydroxide, sodium hydroxide and sodium carbonate, still more preferably lithium hydroxide, in a polar aprotic solvent preferably selected from among tetrahydrofuran, dimethylsulfoxide, N-methylpyrrolidone, dimethylformamide, and dimethylacetamide. Still more preferably, the polar aprotic solvent is tetrahydrofuran.

Step d) of the process of the present invention is carried out through an intermediate of formula VIa

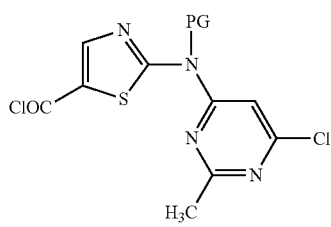

VIa wherein PG is ter-butoxycarbonyl;
obtained by reacting a compound of formula VI with an organic tertiary amine, preferably selected from among triethylamine (TEA), pyridine, N,N-dimethylaminopyridine (DMAP), and N,N-diisopropylethylamine (DIPEA), still more preferably triethylamine, followed by the reaction with a chlorinating agent preferably selected from among oxalylchloride and tionylchloride, in an apolar solvent preferably selected from among methylene chloride, xylene or mixtures thereof. Tionyl chloride in methylene chloride is still more preferably used. The compound VIa is not isolated but is directly used in the subsequent step e).

The reaction between the compound of formula VIa and the compound of formula V is carried out in an apolar solvent preferably selected from among methylene chloride, xylene or mixtures thereof. Methylene chloride is still more preferably used.

Step e) of the process of the present invention is carried out in the presence of a base preferably selected from among sodium carbonate, sodium bicarbonate, potassium carbonate, and potassium bicarbonate. Still more preferably, the base is sodium carbonate. The solvent is an aprotic polar solvent preferably selected from among tetrahydrofuran, dimethylsulfoxide, N-methylpyrrolidone, dimethylformamide, and dimethylacetamide. Still more preferably, the aprotic polar solvent is dimethylsulfoxide.

Under these conditions also the simultaneous deprotection of the compound of formula II, which is then not isolated in the process of the present invention, is obtained.

All the terms used in the present description, unless otherwise indicated, are to be understood in their common meaning as known in the art. Other more specific precise definitions for certain terms, as used in the present description, are highlighted herein after and constantly applied in the whole description and claims, unless a different definition provides specifically a broader meaning.

The term "polar solvent" refers to a solvent which is a proton donor, such as water; an alcohol, for example, methanol, ethanol, propanol, isopropanol, butanol, tert-butanol; or a polarized solvent such as, for example, esters, for example ethylacetate, butyl acetate; nitriles, for example, acetonitrile; ethers, for example, tetrahydrofuran, dioxane; ketones, for example, acetone, methylbutylketone and the like.

Further information about non polar or polar, protic or aprotic solvents can be found in organic chemistry books or in specialized monographs, for example: *Organic Solvents Physical Properties and Methods of Purification*, 4th ed., John A. Riddick, et al., Vol. II, in "*Techniques of Chemistry Series*", John Wiley & Sons, NY, 1986. Such solvents are known to the person skilled in the art and it is moreover clear to the person skilled in the art that different solvents or mixtures thereof can be selected and preferred, depending on the specific compounds and on the reaction conditions, being their choice influenced, for example, by solubility and reagent reactivity, by preferred temperature ranges.

Although the present invention has been described in its characterizing features, the equivalents and modifications obvious to the skilled in the art are included in the present invention.

The present invention will be now illustrated through some examples without limiting the scope of the invention.

EXAMPLE 1

Synthesis of methyl 2-(6-chloro-2-methylpyrimidin-4-yl-amino)thiazol-5-carboxylic acid In a reaction flask, 49.49 g 4,6-dichloro-2-methylpyrimidine (0.303 mol), 40.00 g methyl 2-aminothiazol-5-carboxylic acid (0.253 mol), and 200 ml N,N-dimethylacetamide were charged, the temperature was brought to −5° C. and 18.20 g sodium hydride (0.455 mol) in 90 ml tetrahydrofuran were added dropwise and the reaction mixture was kept under these conditions for about three hours. At the end of the reaction, 250 ml of a solution of hydrochloric acid 2N were added, the temperature was brought to the room value, the formed solid was filtered and washed with water (4×200 ml) and dried in oven under vacuum at a temperature of 55° C. for about eight hours, to give 62.89 g methyl 2-(6-chloro-2-methylpyrimidin-4-yl-amino)thiazol-5-carboxylic acid.

$^1$H-NMR (DMSO, 300 MHz): δ 8.13 (1H, s), 6.97 (1H, s), 3.82 (3H, s), 2.59 (3H, s)

EXAMPLE 2

Synthesis of methyl 2-(ter-butoxycarbonyl-(6-chloro-2-methylpyrimidin-4-ylamino)thiazol-5-carboxylic acid In a reaction flask, 504 ml tetrahydrofuran, 62.89 g methyl 2-(6-chloro-2-methylpyrimidin-4-yl-amino)thiazol-5-carboxylic acid (0.221 mol), 2.56 g N,N-dimethylaminopyridine (0.021 mol) were charged, the temperature was brought to about 25° C. and a solution of 86.82 g di-ter-butyldicarbonate (BOC)$_2$O (0.398 mol) in 126 ml tetrahydrofuran was added dropwise and the reaction mixture was kept under these conditions for about sixteen hours. At the end of the reaction, the mixture was concentrated to residue by distillation under vacuum and 315 ml methylethylketone and 100 ml of a solution of hydrochloric acid 2N were added, the mixture was filtered on celite and the organic phase was washed with a solution of hydrochloric acid 2N (2×100 ml), water (2×150 ml) and with a saturated sodium bicarbonate solution (1×150 ml). The collected organic phases were concentrated to residue by distillation under vacuum and the resultant solid was dried in oven under vacuum at a temperature of about 50° C. for eight hours to give 76.54 g methyl 2-(ter-butoxycarbonyl-(6-chloro-2-methyl-pyrimidin-4-ylamino)thiazol-5-carboxylic acid.

$^1$H-NMR (DMSO, 300 MHz): δ 8.06 (1H, s), 7.98 (1H, s), 3.83 (3H, s), 2.65 (3H, s), 1.43 (9H, s).

EXAMPLE 3

Synthesis of 2-(ter-butoxycarbonyl-(6-chloro-2-methylpyrimidin-4-ylamino)thiazol-5-carboxylic acid In a reaction flask 535 ml tetrahydrofuran, 76.54 g methyl 2-(ter-butoxycarbonyl-(6-chloro-2-methylpyrimidin-4-ylamino)thiazol-5-carboxylic acid (0.199 mol) were added, the temperature was brought to about 30° C. and a solution of 7.15 g lithium hydroxide (0.299 mol) in 230 ml water was added dropwise; the reaction mixture was kept under these conditions for about three hours. At the end of the reaction 320 ml toluene were added and the aqueous phase was washed with toluene (2×321 ml), the temperature was brought to about less than 20° C. and 160 ml of a solution of hydrochloric acid 2N was added. The mixture was filtered, washed with methyltetrahydrofuran (3×87 ml) and the organic phase was then washed with water (4×300 ml). The solvent was removed by distillation under vacuum and the resultant residue was washed with toluene (3×220 ml). The mixture was concentrated to residue by distillation under vacuum to give 75.20 g 2-(ter-butoxycarbonyl-(6-chloro-2-methylpyrimidin-4-ylamino)thiazol-5-carboxylic acid.

$^1$H-NMR (DMSO, 300 MHz): δ 7.95 (2H, s), 2.64 (3H, s), 1.47 (9H, s).

EXAMPLE 4

Synthesis of ter-butyl-6-chloro-2-methylpyrimidin-4-yl-(5-(2-chloro-6-methylphenyl-carbamoyl)thiazol-2-yl)carbamate In a reaction flask 54.88 g 22-(ter-butoxycarbonyl-(6-chloro-2-methylpyrimidin-4-ylamino)thiazol-5-carboxylic acid (0.148 mol), 80.85 g triethylamine (0.740 mol), 376 ml dichloromethane were charged, the temperature was brought to about 0° C. and 22.89 g thionyl chloride (0.192 mol) were added dropwise, the temperature was brought to about 25° C. and the reaction mixture was kept under these conditions for about two hours. The temperature was brought to about 15° C., 25.20 g 2-chloro-6-methylaniline (0.178 mol) were added, the temperature was brought to about 25° C. and the reaction mixture was kept under these condition for about 16 hours. At the end of the reaction, 200 ml demineralized water were added and the organic phase was washed with demineralized water (2×200 ml), hydrochloric acid solution 2N (2×200 ml), sodium bicarbonate solution 5% (2×200 ml), demineralized water (200 ml) and a saturated sodium chloride solution (200 ml). The collected organic phases were concentrated to residue to give 56.70 g ter-butyl-6-chloro-2-methylpyrimidin-4-yl-(5-(2-chloro-6-methylphenylcarbamoyl)thiazol-2-yl)carbamate.

$^1$H-NMR (DMSO, 300 MHz): δ 10.02 (1H, s), 8.32 (1H, s), 7.42 (1H, d), 7.28 (2H, m), 6.95 (1H, s), 2.65 (3H, s), 2.25 (3H, s).

EXAMPLE 5

Synthesis of Dasatinib

In a reaction flask 283.5 ml dimethylsulfoxide, 29.83 g 1-(2-hydroxyethyl)piperazine (0.229 mol), 12.08 g sodium carbonate (0.144 mol), 56.70 g ter-butyl-6-chloro-2-methylpyrimidin-4-yl-(5-(2-chloro-6-methylphenylcarbamoyl)thiazol-2-yl)carbamate (0.114 mol) were charged at a temperature of about 25° C. and the reaction mixture was kept under these conditions for about five hours. At the end of the reaction, 760 ml water were added, the mixture was kept under stirring for about 30 minutes and the formed solid was filtered, washed with water (4×260 ml) and suspended in 440 ml methanol. 42.88 g di-terbutylamine (DBTA, 0.120 mol) were added, the temperature was brought to the solvent reflux value and 15.19 g tromethamol (TRIZMA) (0.125 mol) were added. The temperature was brought to about 25° C. and the formed solid was filtered, washed with methanol (2×45 ml) and dried in oven under vacuum at a temperature of about 50° C. for eight hours to give 44.51 g dasatinib.

The invention claimed is:
1. A process for the synthesis of dasatinib, comprising:
a) reacting the compound of formula X

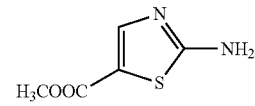

with the compound of formula IX

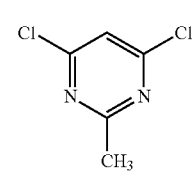

in an aprotic polar solvent and in the presence of a base, to give the compound of formula VIII

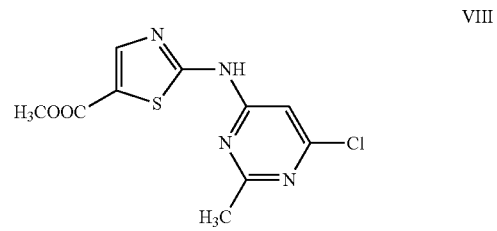

b) a protecting reaction of the compound of formula VIII to give a compound of formula VII

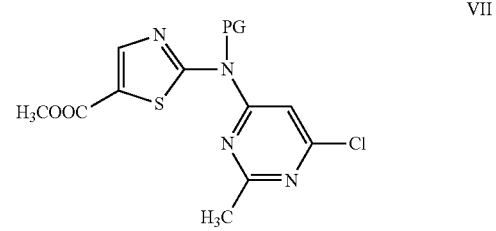

wherein PG is an amine protecting group;
c) a hydrolysis reaction of a compound of formula VII to give a compound of formula VI

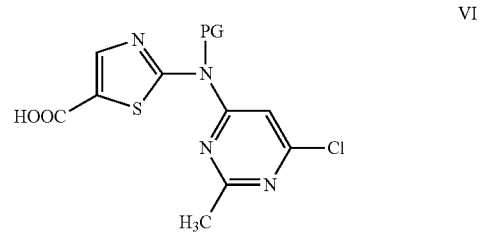

wherein PG is an amine protecting group;

d) reacting of a compound of formula VI with the compound of formula V

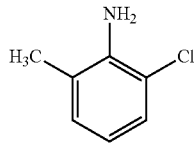

to give a compound of formula IV

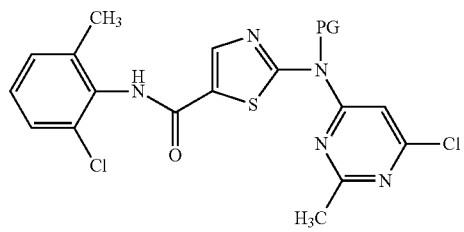

wherein PG is an amine protecting group;
e) a coupling reaction of a compound of formula IV

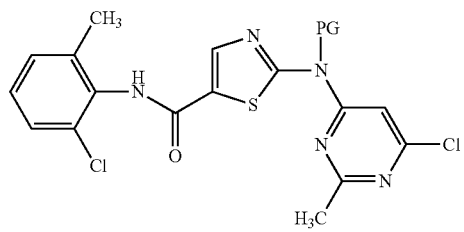

wherein PG is an amine protecting group,
with the compound of formula III

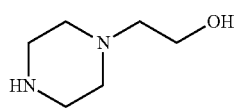

in the presence of a base in a suitable solvent to give a compound of formula II

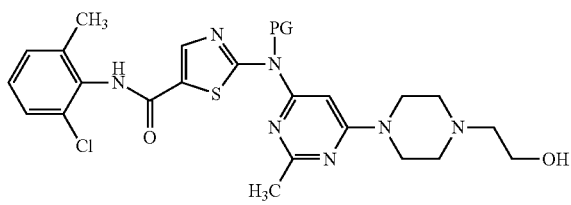

wherein PG is an amine protecting group;
and the simultaneous deprotection of said compound of formula II to give dasatinib of formula I or a salt thereof

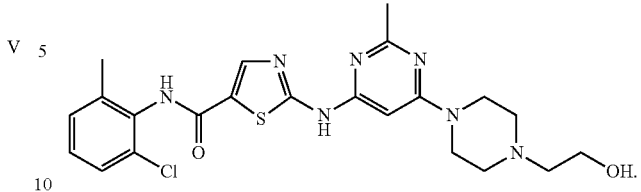

2. A process according to claim 1 wherein PG is ter-butoxycarbonyl.

3. A process according to claim 1, wherein in step a) the aprotic polar solvent is selected from the group consisting of N-methylpyrrolidone, dimethylacetamide, dimethylformamide, tetrahydrofuran, methyl-tetrahydrofuran and mixtures thereof; and the base is selected from the group consisting of sodium hydride, potassium hydride, and lithium hydride.

4. A process according to claim 1, wherein in step b) the base is selected from the group consisting of N,N-dimethylaminopyridine, 1,5,7-triazabicyclo[4.4.0]dec-5-ene, 1,4-diazabicyclo[2.2.2]octane, and 1,5-diazabicyclo[5.4.0]undec-5-ene; in a polar solvent selected from the group consisting of tetrahydrofuran, methyl-tetrahydrofuran, acetonitrile, dimethylformamide, dimethylacetamide, N-methylpyrrolidone, dimethylsulfoxide, and mixtures thereof; or in an apolar solvent selected from the group consisting of toluene, xylene and mixtures thereof.

5. A process according to claim 1 wherein step c) is carried out in the presence of an inorganic base selected from the group consisting of lithium hydroxide, sodium hydroxide and sodium carbonate, in an aprotic polar solvent selected from the group consisting of tetrahydrofuran, dimethylsulfoxide, N-methylpyrrolidone, dimethylformamide, and dimethylacetamide.

6. A process according to claim 1 wherein step d) is carried out through an intermediate of formula VIa

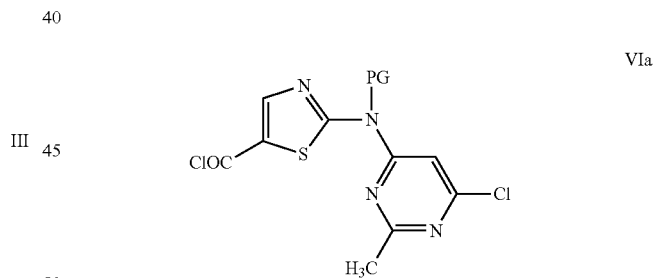

wherein PG is an amine protecting group;
obtained by reaction of a compound of formula VI with a tertiary organic amine selected from the group consisting of triethylamine, pyridine, and N,N-diisopropylethylamine, followed by the reaction with a chlorinating agent selected from the group consisting of oxalyl chloride and thionyl chloride, in an apolar solvent selected from the group consisting of dichloromethane, xylene and mixtures thereof, followed by reaction of the compound of formula VIa and the compound of formula V in an apolar solvent selected from the group consisting of dichloromethane and xylene and mixtures thereof.

7. A process according to claim 1 wherein in step e) the base is selected from the group consisting of sodium carbonate, sodium bicarbonate, potassium carbonate, and potassium bicarbonate, in an aprotic polar solvent selected from the group consisting of tetrahydrofuran, dimethylsulfoxide, N-methylpyrrolidone, dimethylformamide, and dimethylacetamide.
8. The compounds
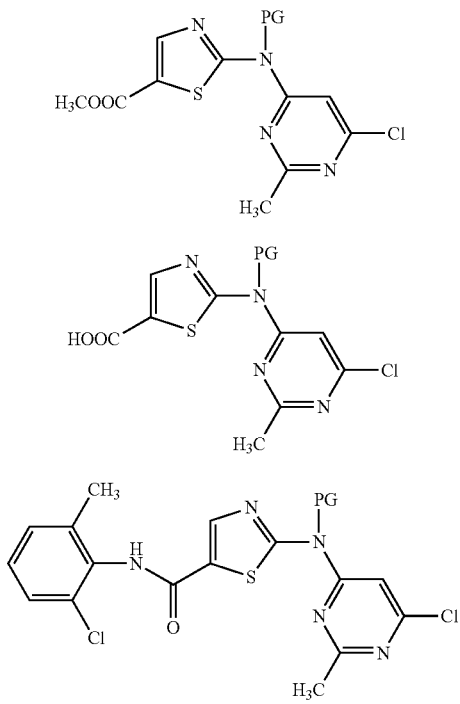
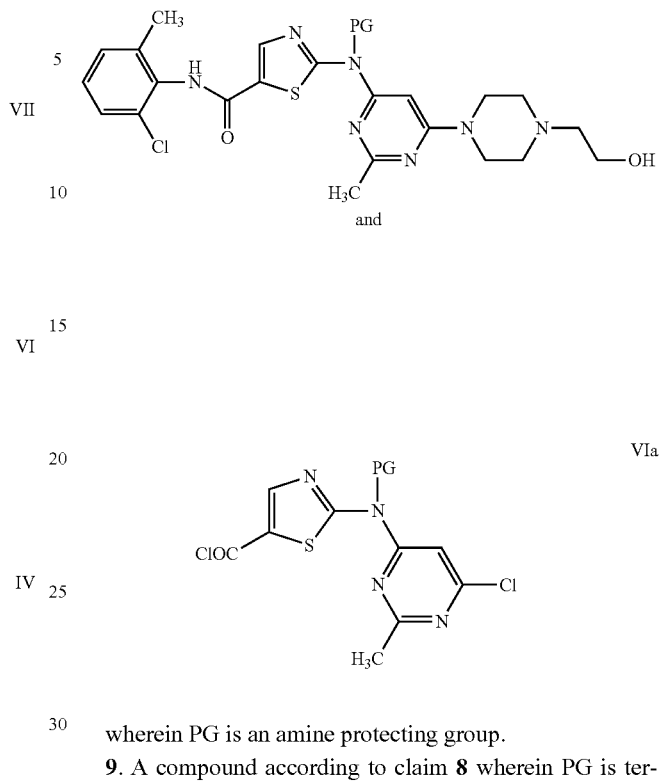
wherein PG is an amine protecting group.
9. A compound according to claim 8 wherein PG is ter-butoxycarbonyl.
* * * * *